United States Patent [19]

Park

[11] Patent Number: 5,518,714
[45] Date of Patent: May 21, 1996

[54] METHOD FOR INHIBITING THE DISSOLUTION OF ANTIPERSPIRANT COMPOUNDS IN ALCOHOLS

[75] Inventor: Andrew C. Park, Merseyside, England

[73] Assignee: Chesebrough-Pond's USA Co., Division of Conopco, Inc., Greenwich, Conn.

[21] Appl. No.: 725,681

[22] Filed: Apr. 22, 1985

[30] Foreign Application Priority Data

Apr. 24, 1984 [GB] United Kingdom ............... 8410403

[51] Int. Cl.[6] .................. A61K 7/32; A61K 7/34; A61K 7/36; A61K 7/38
[52] U.S. Cl. ................ 424/65; 424/66; 424/67; 424/68; 424/47
[58] Field of Search ................ 424/65, 66, 67, 424/68, 47

[56] References Cited

U.S. PATENT DOCUMENTS

| | | | |
|---|---|---|---|
| 2,230,082 | 1/1941 | Montenier | 424/68 |
| 2,236,387 | 3/1941 | Wallace et al. | 424/68 |
| 2,586,287 | 2/1952 | Apperson et al. | 424/68 |
| 2,736,683 | 2/1956 | Apperson et al. | 424/68 |
| 2,791,486 | 5/1957 | Appell | 424/68 X |
| 2,814,584 | 11/1957 | Daley | 424/66 |
| 2,814,585 | 11/1957 | Daley | 424/68 |
| 2,955,983 | 10/1960 | Messina | 424/68 |
| 3,198,708 | 8/1965 | Henkin et al. | 424/68 |
| 3,211,620 | 10/1965 | Henkin et al. | 424/68 |
| 3,792,068 | 2/1974 | Luedders et al. | 424/47 |
| 3,932,609 | 1/1976 | Rosenstreich et al. | 424/68 |
| 3,968,203 | 7/1976 | Spitzer et al. | 424/47 |
| 4,028,390 | 6/1977 | Rubino et al. | 556/27 |
| 4,108,977 | 8/1978 | Kenkare et al. | 424/68 |
| 4,113,852 | 9/1978 | Kenkare et al. | 424/68 |
| 4,359,456 | 11/1982 | Gosling et al. | 424/68 |
| 4,435,382 | 3/1984 | Shin et al. | 424/66 |

FOREIGN PATENT DOCUMENTS

| | | |
|---|---|---|
| 1119960 | 3/1982 | Canada. |
| 1146073 | 5/1983 | Canada. |
| 6738 | 9/1980 | European Pat. Off.. |
| 28853 | 5/1981 | European Pat. Off.. |
| 0070517 | 1/1983 | European Pat. Off.. |
| 113121 | 7/1983 | Japan. |
| 753576 | 6/1975 | South Africa. |
| 1192021 | 3/1970 | United Kingdom. |
| 2018590 | 10/1979 | United Kingdom. |
| 2048229 | 12/1980 | United Kingdom. |
| 1597497 | 9/1981 | United Kingdom. |
| 2144992 | 3/1985 | United Kingdom. |

OTHER PUBLICATIONS

ICI—Technical Bulletin, Antiperspirants and Deodorants, Sep. 1982, pp. 6 and 7.
Kirk–Othmer's Encyclopaedia of Chemical Technology, Second Edition vl. 7, (1965) pp. 378–396.

*Primary Examiner*—C. Warren Ivy
*Assistant Examiner*—D. Margaret M. Mach
*Attorney, Agent, or Firm*—Gerard J. McGowan, Jr.

[57] ABSTRACT

A method of inhibiting the dissolution in anhydrous ethanol or isopropanol of a powdered aluminium-containing basic halide antiperspirant agent which comprises incorporating in the ethanol or isopropanol an amount effective to inhibit said dissolution of an alcohol soluble or alcohol-insoluble dissolution-inhibiting compound selected from the group consisting of compounds having a basic nitrogen function and compounds having a basic oxygen function. Examples of dissolution-inhibiting compounds are urea, thiorea, amino acids, $C_1$–$C_{20}$ alkylamines and hydroxyalklyamines, inorganic bases, and alkali metal and alkaline-earth metal salts of inorganic acids and $C_1$–$C_{20}$ organic carboxylic acids. The dissolution-inhibiting compound may alternatively be a particulate alcohol-insoluble inorganic drying agent such as a molecular sieve.

1 Claim, No Drawings

METHOD FOR INHIBITING THE DISSOLUTION OF ANTIPERSPIRANT COMPOUNDS IN ALCOHOLS

This invention relates to methods for formulating antiperspirants and more particularly although not exclusively to the formulations of antiperspirant compositions suitable for dispensing from a roll-on dispenser.

Practically all antiperspirant roll-on compositions consist of either an emulsion in an oil of an aqueous solution of an antiperspirant agent, or a thickened solution of an antiperspirant agent in an aqueous alcoholic vehicle. The only commercially available roll-on products of which the applicant is aware wherein the active antiperspirant agent is in powder form suspended in a non-aqueous vehicle are those in which the vehicle consists essentially of a silicone or mixture of silicones. Such products are of the types described in British Patent No. 2 018 590 (Gillette) and European Patent No. 28,853 (Procter & Gamble), respectively. Such products are expensive to formulate due to the cost of the silicone ingredients which represent the major component of the respective formulations.

It has, however, been suggested in the patent literature to formulate roll-on antiperspirant compositions in the form of a suspension of the antiperspirant active compound in a substantially anhydrous vehicle consisting solely or primarily of ethanol or isopropanol. Such types of composition are described in British Patent No. 1 192 021 (Unilever) and Canadian Patent No. 1 146 073 (Bristol-Myers). In the British patent the active antiperspirant agent is aluminium chlorhydrate and in the Canadian patent the active agent is one of a number of specified glycine complexes of aluminium-containing basic chlorides.

Although aluminium chlorhydrate and the glycine complexes are generally considered as insoluble in alcohol, they do nevertheless slowly dissolve as can be shown, for example, by measuring the amount of aluminium that passes into solution from these aluminium-containing antiperspirant active agents.

As well as for antiperspirant roll-on products comprising a suspension of a particulate aluminium-containing basic halide in ethanol or isopropanol, it is also desirable to inhibit the dissolution in alcohol of particulate antiperspirant actives in the case of antiperspirant suspension type aerosol products wherein the liquid medium in which antiperspirant powder is suspended (excluding the propellant) comprises at least a substantial proportion of anhydrous ethanol or isopropanol. Aerosol products of this kind are described in South African Patent 75/3576 (Colgate Palmolive).

It is an object of the present invention to provide a method of reducing the solubility in ethanol and isopropanol of various antiperspirant compounds.

The present invention is based on the surprising finding that the dissolution of certain antiperspirant active agents in the above alcohols can be inhibited by including relatively small amounts of certain compounds in the alcohol.

According to one aspect of the present invention there is provided a method of inhibiting the dissolution in anhydrous ethanol or isopropanol of a powdered aluminium-containing basic halide antiperspirant agent which comprises incorporating in the ethanol or isopropanol an amount effective to inhibit said dissolution of an alcohol soluble or alcohol-insoluble dissolution-inhibiting compound selected from the group consisting of compounds having a basic nitrogen function and compounds having a basic oxygen function.

By "anhydrous" ethanol or isopropanol is meant hereinafter ethanol or isopropanol, respectively, containing less than 1% by weight water.

The antiperspirant active agent employed in the method of the invention may be a basic aluminium chloride having an aluminium to chlorine molar ratio of 1:1 to 2.5:1, more especially aluminium chlorhydrate wherein said ratio is from 1.9:1 to 2.1:1; basic aluminium bromides having an aluminium to bromine molar ratio of 1:1 to 2.5:1 more particularly 1.9:1 to 2.1:1, an aluminium zirconium chlorhydrate, for example aluminium zirconium trichlorhydrate, aluminium zirconium tetrachlorhydrate, aluminium zirconium pentachlorhydrate, and aluminium zirconium octachlorhydrate (these are CTFA generic names); and any of the previously named compounds complexed with urea or glycine, for example aluminium zirconium sesquichlorhydrate glycine complex, aluminium zirconium trichlorhydrate glycine complex and aluminium zirconium tetrachlorhyrate glycine complex. Methods for preparing aluminium zirconium chlorhydrates are described in, for example, U.S. Pat. No. 4,028,390 (Armour) and U.S. Pat. No. 3,792,068 (Procter & Gamble), the disclosures of which are incorporated herein by reference. Suitable aluminium zirconium chlorhydrate powders for use in the antiperspirant compositions of this invention are available from the Reheis Chemical Company under the trade names REZAL 36GP and REZAL 67P (REZAL is a trade mark) and from Wickhen Products Incorporated under the trade names WICKENOL 369 and WICKENOL 379 and WICKENOL 373 (WICKENOL is a trade mark). The basic aluminium chloride antiperspirant active materials may be those having a particular distribution of polymeric species in aqueous solution and obtainable by procedures described in U.S. Pat. No. 4,359,456 (Gosling et al). Similar processes for making more highly active forms of aluminium chlorhydrate involving the ageing of aluminium chlorhydrate in an aqueous medium are described in British Patent Specification No. 2 048 229 (Gillette). The antiperspirant agent may also be a urea or glycine complex of aluminium chlorhydrate prepared as described in European Patent No. 6738 (Unilever) and British Patent No. 1 597 497 (Unilever), respectively, the disclosures of which patents are incorporated herein by reference The amount of the particulate antiperspirant compound which is suspended in the ethanol or isopropanol in a typical roll-on composition is 1 to 50%, preferably 5–40%, more usually 8 to 30% by weight of the total composition.

The anti-dissolution agent is selected from the group of compounds having a basic nitrogen function or a basic oxygen function.

Examples of compounds having a basic nitrogen function are urea and thiourea; amino acids for example glycine, alanine, taurine, serine, sarcosine, valine, leucine, proline, methionine, threonine, arginine, ornithine, lysine, lysine monohydrochloride, glutamic acid monomethyl ester (which amino acids include the neutral amino acids and the basic amino acids); and the $C_1$–$C_{20}$ alkylamines and hydroxyalkylamines, for example triethylamine, mixed $C_{13}$/$C_{15}$ alkylamine and 2-amino-2-methyl-propan-1-ol.

Examples of compounds having a basic oxygen atom are inorganic bases such as the hydroxides of the alkali metal and the alkaline-earth metals and ammonium hydroxide, including sodium hydroxide, potassium hydroxide, lithium hydroxide, calcium hydroxide and magnesium hydroxide, as well as the basic metallic oxides, for example zinc oxide and lanthanum oxide; and the alkali metal salts and alkaline-earth metal salts of inorganic acids, for example sodium carbonate, sodium tetraborate, sodium thiosulphate and dipotassium hydrogen orthophosphate, and of $C_1$–$C_{20}$ organic carboxylic acids for example sodium acetate, trisodium citrate, sodium n-octanoate and sodium stearate.

An appropriate amount of the anti-dissolution agent is simply incorporated into the alcohol prior to the addition of the powdered antiperspirant agent or together with it. It is less satisfactory to include it afterwards.

The amount of the anti-dissolution agent is that which is effective to inhibit dissolution of the powdered antiperspirant compound in the alcohol. The amount required will depend on the particular inhibitor employed. Generally speaking a satisfactory amount will be from about 0.1 to about 25% by weight of the ethanol or isopropanol. The amount of urea, thiourea or amino acid will generally be in the range of about 0.5 to about 25% by weight of the alcohol although in practice any amount can be included which is consistent with an acceptable product. The alkylamines and hydroxyalkylamines are used in an amount of about 0.5 to about 4% by weight of the alcohol. The alkali metal inorganic bases and ammonium hydroxide are suitably used in amounts of about 0.1 to about 2% by weight of the alcohol and other inorganic bases, basic oxides and inorganic acid salts in amounts of about 0.5 to 10% by weight of the alcohol. The salts of the $C_1$–$C_{20}$ carboxylic acids may be used in an amount of about 1 to about 20% by weight of the alcohol.

According to a second aspect of the invention there is provided a method of inhibiting the dissolution in anhydrous ethanol or isopropanol of a powdered aluminium-containing basic halide antiperspirant agent which comprises incorporating in the ethanol or isopropanol an amount effective to inhibit said dissolution of a particulate alcohol-insoluble inorganic drying agent. Examples of suitable inorganic drying agents are anhydrous sodium sulphate and molecular sieves, for example the material known as Molecular Sieve Type 3A. Other inorganic drying agents are described in Kirk-Othmer's Encyclopedia of Chemical Technology, 2nd Edition, Vol 7 (1965) pages 378 to 396, the disclosure of which is incorporated herein by reference. Any drying agent which is compatible with the alcohol is suitable. Effective amounts of the drying agent for the inhibition of dissolution of the antiperspirant agent will be found in the range 1 to 20% by weight of the alcohol.

Having formed a more stable suspension of the antiperspirant agent in ethanol or isopropanol in accordance with the invention, the formulation of a satisfactory antiperspirant composition is essentially completed by the further inclusion of a suitable suspending agent for maintaining the antiperspirant agent in suspended form for prolonged periods of time. Suitable suspending agents are well known to those skilled in the art. Preferred suspending agents are the hydrophobic montmorillonite or hectorite clays which are commercially available under the trade name BENTONE from National Lead. Other useful suspending agents are the fine silica powders especially the fumed silicas available commercially under the names AEROSIL and CAB-O-SIL.

Other ingredients may be included as generally known in the art. A proportion of an emollient oil may be included and a perfume is a usual ingredient.

The following experiments illustrate the invention. Percentages are by weight.

EXPERIMENT 1

To saturated solutions of urea in anhydrous ethanol (urea concentration about 5.4% w/w) were added various antiperspirant active materials in an amount of 25% w/w. The compositions were mixed for 48 hours at 20° C. The concentration of aluminium in the liquid phase was then determined by analysis using atomic absorption spectroscopy. Such concentrations are expressed herein as M which stands for moles of aluminium per liter of ethanolic solution. The anhydrous ethanol was a grade of absolute alcohol containing a maximum amount of water of 0.3% by weight.

The results for various antiperspirant active agents are given in Table 1.

TABLE 1

| Active | M | |
|---|---|---|
| | No urea | Urea |
| Aluminium chlorhydrate | 1.374 | 0.083 |
| Aluminium zirconium tetra chlorhydrate glycine complex[1] | 0.011 | 0.001 |
| Aluminium zirconium pentachlorhydrate[2] | 1.637 | 0.004 |
| Aluminium zirconium trichlorhydrate[3] | 1.376 | 0.011 |
| Basic aluminium bromide[4] | 1.844 | 0.715 |
| Aluminium chlorhydrate urea complex[5] | 0.030 | 0.001 |

[1]- REZAL 36GP
[2]- REZAL 67P
[3]- REZAL 36P
[4]- 2 hour test period
[5]- according to European Patent No. 6738

For all the actives, the presence of the urea effected a substantial reduction in the amount of the active passing into solution in the alcohol.

EXPERIMENT 2

In this experiment the effect of varying the amount of urea on the extent of dissolution in anhydrous ethanol of two antiperspirant agents is illustrated.

TABLE 2

| | M | |
|---|---|---|
| Amount of Urea % (w/w) | Aluminium chlorhydrate | Aluminium zirconium trichlorhydrate |
| 0 | 1.374 | 1.376 |
| 1 | 0.617 | 0.128 |
| 3 | 0.259 | 0.067 |
| 4 | 0.180 | 0.013 |
| 5.4 | 0.083 | 0.011 |
| 10.8 | 0.002 | 0.004 |

EXPERIMENT 3

In this experiment the effect of other additives in inhibiting the dissolution of aluminium chlorhydrate anydrous ethanol was demonstrated, the results being summarised in Table 3.

TABLE 3

| Additive | Amount of Additive % (w/w) | M |
|---|---|---|
| Glycine | 5 | 0.015 |
| Leucine | 5 | 0.012 |
| L-Histidine | 5 | 0.002 |
| L-Lysine hydrochloride | 5 | 0.015 |
| L-Arginine | 5 | 0.002 |
| Triethylamine | 2 | 0.001 |
| Mixed $C_{13}$/$C_{15}$ amine | 2 | 0.009 |

TABLE 3-continued

| Additive | Amount of Additive % (w/w) | M |
|---|---|---|
| 2-Amino-2-methyl propan-1-ol | 3 | 0.012 |
| Sodium hydroxide | 1 | 0.001 |
| Calcium hydroxide | 1 | 0.003 |
| Ammonium hydroxide | 1 | 0.022 |
| Zinc oxide | 5 | 0.001 |
| Sodium acetate | 5 | 0.006 |
| Trisodium citrate | 5 | 0.003 |
| Sodium n-octanoate | 5 | 0.095 |
| Sodium stearate | 5 | 0.042 |
| Sodium carbonate | 2 | 0.178 |
| Sodium thiosulphate | 5 | 0.276 |
| Sodium tetraborate | 5 | 0.013 |
| Dipotassium hydrogen orthophosphate | 5 | 0.159 |
| Sodium sulphate (anhydrous) | 5 | 0.666 |
| Molecular Sieve Type 3A | 5 | 0.003 |
| No additive | — | 1.374 |

EXPERIMENT 4

In this experiment the effect of additives other than urea in inhibiting the dissolution of aluminium zirconium trichlorhydrate in anhydrous ethanol was shown, the results being given in Table 4.

TABLE 4

| Additive | Amount of Additive % (w/w) | M |
|---|---|---|
| Glycine | 5 | 0.001 |
| Leucine | 5 | 0.264 |
| Triethylamine | 2 | 0.008 |
| Mixed $C_{13}/C_{15}$ amine | 2 | 0.756 |
| 2-amino-2-methyl-propan-1-ol | 3 | 0.025 |
| Sodium hydroxide | 1 | 0.078 |
| Calcium hydroxide | 5 | 0.001 |
| Ammonium hydroxide | 5 | 0.007 |
| Sodium acetate | 5 | 0.092 |
| Trisodium citrate | 5 | 0.001 |
| Sodium sulphate (anhydrous) | 5 | 0.492 |
| Molecular Sieve Type 3A | 5 | 0.138 |
| No additive | — | 1.376 |

EXPERIMENT 5

In this experiment the effect of additives in inhibiting the dissolution of aluminium zirconium trichlorhydrate in anhydrous isopropanol was shown, the results being given in Table 5.

TABLE 5

| Additive | Amount of Additive % (w/w) | M |
|---|---|---|
| Urea | 2 | 0.008 |
| Glycine | 5 | 0.000 |
| L-Arginine | 5 | 0.003 |
| L-Aspartic acid[1] | 5 | 0.324 |
| Calcium hydroxide | 5 | 0.000 |
| Mixed $C_{13}/C_{15}$ amine | 2 | 0.003 |
| 2-amino-2-methyl propan-1-ol | 2 | 0.001 |
| Sodium acetate | 5 | 0.001 |
| Molecular Sieve Type 3A | 5 | 0.000 |
| No additive | — | 0.018 |

TABLE 5-continued

| Additive | Amount of Additive % (w/w) | M |
|---|---|---|

[1]- a comparative test showing no inhibitive effect when using an acidic amino acid

EXPERIMENT 6

Various other compounds that have been shown to be ineffective for inhibiting the dissolution of aluminium chlorhydrate in ethanol are referred to in Table 6.

TABLE 6

| Additive | % (w/w) | M |
|---|---|---|
| Acetamide | 3 | 2.052 |
| Coconut diethanolamide | 3 | 1.175 |
| Cetyl trimethylammonium bromide | 5 | 2.230 |
| Ammonium thiocyanate | 5 | 1.550 |
| Sodium chloride | 2 | 1.267 |
| Sodium bromide | 2 | 1.550 |
| Sodium iodide | 5 | 1.757 |
| Citric acid | 5 | 2.323 |
| Isopropyl myristate | 10 | 1.256 |
| Cyclic volatile silicone | 10 | 1.111 |
| Dipropylene glycol methyl ether | 10 | 1.215 |
| Butylene glycol | 10 | 1.674 |
| No additive | — | 1.374 |

The following are Examples of antiperspirant roll-on lotions prepared according to the invention. Percentages are by weight.

| | % | | | | | |
|---|---|---|---|---|---|---|
| Examples: | 1 | 2 | 3 | 4 | 5 | 6 |
| AACH[1] | 25.0 | 25.0 | 20.0 | — | 10.0 | — |
| Rezal 36GP[3] | — | — | — | 20.0 | 15.0 | 25.0 |
| Ethanol (anhydrous) | 60.8 | — | 67.4 | 70.0 | — | 60.8 |
| Isopropanol (anhydrous) | — | 62.7 | — | — | 60.8 | — |
| Bentone 38 | 10.0 | 10.0 | 8.0 | 8.0 | — | 10.0 |
| Bentone 27 | — | — | — | — | 10.0 | — |
| Perfume | 1.0 | 1.0 | 1.0 | 1.0 | 1.0 | 1.0 |
| Urea | 3.2 | 1.3 | 3.6 | 1.0 | 3.2 | 3.2 |

| | % | | | | | |
|---|---|---|---|---|---|---|
| Examples: | 7 | 8 | 9 | 10 | 11 | 12 |
| AACH[1] | 25.0 | — | — | — | — | — |
| AACH/Urea complex[2] | — | 25.0 | 20.0 | — | — | — |
| ACH[4] | — | — | — | 25.0 | 25.0 | 20.0 |
| Ethanol (anhydrous) | 51.3 | 58.0 | 51.5 | 61.5 | 63.5 | 68.0 |
| VS 7207[5] | 10.0 | — | — | — | — | — |
| DPGME[6] | — | 8.0 | 18.0 | — | — | — |
| Bentone 38 | 10.0 | 7.0 | 9.0 | 10.0 | 10.0 | 8.0 |
| Perfume | 1.0 | 1.0 | 1.0 | 1.0 | 1.0 | 1.0 |
| Urea | 2.7 | 1.0 | 0.5 | 2.5 | — | — |
| Sodium hydroxide | — | — | — | — | 0.5 | — |
| Trisodium citrate | — | — | — | — | — | 3.0 |

[1]- Spray-dried powder of an activated aluminium chlorhydrate prepared according to U.S. Pat. No. 4 359 456. It had a particle size of less than 75 microns. It has a Band III percent Aluminium Value of greater than 20%.
[2]- This is a preformed complex of urea and an activated aluminium chlorhydrate (AACH) prepared by codissolving AACH and urea (mole ratio 2:1) in water and spray drying the solution.

-continued

3- Aluminium zirconium tetrachlorhydrate glycine complex available from Reheis Chemical Company. It has a particle size of less than 53 microns (at least 98.5% less than 44 microns).
4- Aluminium chlorhydrate available from Reheis Chemical Company under the trade mark MICRODRY.
5- A cyclic polydimethylsiloxane mainly tetramer available from Union Carbide.
6- Dipropylene glycol methyl ether available from Dow Chemical under the trade name Dowanol DPM.

The products of the Examples are made by shearing the suspending agent in the liquid component or mixture of the liquid components, excluding the perfume, until fully dispersed. The urea, sodium hydroxide and the trisodium citrate were added to the alcohol prior to the addition of the antiperspirant powder. The antiperspirant powder and perfume are then added and dispersed by further high shear mixing. The product is then filled into roll-on dispensers.

The products of Examples 1 and 2 were assessed by the following test procedure involving subjecting human volunteers to thermal stress and gravimetric determination of axilla sweat.

Subjects

A panel of up to 60 women who use no antiperspirant for the 14 days before the test.

Hot Room

Temperatures 40° C.±2° C.; relative humidity 40%±5%.

Products

Two products of which one is designated the control. The panel is divided into two equal groups. One group receives the test treatment on the left axilla and the control treatment on the right, while the second group receives them the other way round.

Control Product

Placebo deodorant. This was an aerosol product comprising 25% ethanol, 0.6% isopropyl myristate, 0.3% perfume, and 74.1% propellant (1:1 mixture of Propellants 11 & 12).

Product Application

The operator conducting the test applies the test product in the normal way so as to deposit an appropriate quantity of product eg. on average about 300 mg of product.

Sweat Collection

Absorbent cotton pads are used to collect the sweat. On entering the hot room each panellist is subjected to a 40 minute 'warm-up' period, during which no sweat is collected. Sweat is then collected for a 20 minute period and sweat weight determined.

Test Design

Subjects attend daily for 3 consecutive days. They receive one treatment with the products on each of the first three days. Following product application on the third day, the panellist is subjected to a hot room sitting and sweat collection.

Analysis of Data

The statistical treatment includes an analysis of variance which allows for panellist side and product effects. The efficacy is calculated from the geometric mean weight of sweat collected from the axillae treated with each product using the formula $$\% \text{ reduction} = 100 \frac{(C-T)}{C}$$

where C is the geometric mean sweat weight from the axillae treated with the control product and T is the geometric mean sweat weight from the axillae treated with the test product where a correction has been made for the side effect.

The results of tests conducted with each of the products of Examples 1, 2 and 6 gave sweat reductions as indicated below.

| Product | % Sweat Reduction |
| --- | --- |
| Example 1 | 58 |
| Example 2 | 53 |
| Example 6 | 58 |

The products of all of Examples 1 to 12 are stable antiperspirant lotions which dry quickly to form a structured, tenacious film on the skin. The urea present acts as an anti-dissolution agent enhancing stability of the active antiperspirant agent. It can also improve the structure imparted by the Bentone and allow less of the suspending agent to be used. The DPGME present in Examples 8 and 9 results in a less white deposit on the skin.

EXAMPLE 13

The following is the formulation of an aerosol product made according to the invention.

|  | % |
| --- | --- |
| Aluminium chlorhydrate | 3.5 |
| Anhydrous ethanol | 9.5 |
| Bentone 27 | 0.5 |
| Propylene carbonate | 0.165 |
| Urea | 0.5 |
| Perfume | 0.2 |
| Propellant[1] | to 100.0 |

1- mixture of 35 parts dichlorodifluoromethane and 65 parts trichloromonofluoromethane.

The Bentone 27 is sheared in the mixture of the liquid components, excluding the propellant and perfume, until fully dispersed. The urea is pre-dissolved in the alcohol. The aluminium chlorhydrate and perfume are then added. The resulting concentrate is then placed in a can, sealed with a suitable aerosol valve, and pressurised with the propellant.

This application is related to concurrently filed Park Application S/N 725,699, entitled "Antiperspirant Product", the disclosure of which is incorporated herein by reference.

What is claimed is:

1. A method of inhibiting the dissolution in an anhydrous alcohol selected from the group consisting of ethanol and isopropanol, of a powdered aluminum-containing basic halide antiperspirant agent, which method comprises the step of incorporating in the anhydrous alcohol the powdered antiperspirant agent and an amount effective to inhibit said dissolution from about 0.1 to about 25% by weight of the alcohol, of an alcohol-soluble or alcohol-insoluble dissolution-inhibiting compound selected from the group consisting of (a) compounds having a basic nitrogen function selected from the group consisting of urea, thiourea, glycine, alanine, taurine, serine, sarcosine, valine, leucine, proline, methionine, threonine, arginine, ornithine, lysine, lysine monohydrochloride, glutamic acid monomethyl ester, $C_1$ to $C_{20}$ alkylamines and hydroxylalkylamines, mixed $C_{13}/C_{15}$ alkylamines and 2-amino-2-methyl-propan-1-ol and (b) compounds having a basic oxygen function selected from the group consisting of ammonium hydroxide, sodium hydroxide, potassium hydroxide, lithium hydroxide, calcium hydroxide, magnesium hydroxide, zinc oxide, lanthanum oxide, sodium carbonate, sodium tetraborate, sodium thiosulfate, dipotassium hydrogen orthophosphate, sodium acetate, trisodium citrate, sodium n-octanoate and sodium stearate the dissolution inhibitor and the powdered antiperspirant agent being incorporated substantially at the same time in the ethanol or isopropanol.

* * * * *